United States Patent
Barnes et al.

(10) Patent No.: US 7,826,654 B2
(45) Date of Patent: Nov. 2, 2010

(54) PAINTING PROCESS COLOR COMPENSATOR

(75) Inventors: Thomas Henry Barnes, Austin, TX (US); John W. Dunsmoir, Round Rock, TX (US); Sheryl S. Kinstler, Dripping Springs, TX (US); Mei Yang Selvage, Pocatello, ID (US); Abigail Alice Tittizer, Austin, TX (US); Carol Sue Robertson Walton, Austin, TX (US)

(73) Assignee: International Business Machines Corporation, Armonk, NY (US)

( * ) Notice: Subject to any disclaimer, the term of this patent is extended or adjusted under 35 U.S.C. 154(b) by 134 days.

(21) Appl. No.: 12/157,245

(22) Filed: Jun. 9, 2008

(65) Prior Publication Data

US 2008/0247631 A1     Oct. 9, 2008

(51) Int. Cl.
*G06K 9/00*     (2006.01)

(52) U.S. Cl. ...................................... 382/141
(58) Field of Classification Search ................. 382/141
See application file for complete search history.

*Primary Examiner*—Charles Kim
*Assistant Examiner*—Nirav G Patel
(74) *Attorney, Agent, or Firm*—David A. Mims, Jr.; William Steinberg; Robert V. Wilder (57) ABSTRACT

A method and implementing computer system are provided for enabling a user to paint a surface a desired final color while using a paint, the color of which appears in raw form different from the desired final color for the painted surface. In an exemplary embodiment, a tile painting application is illustrated and includes a camera arranged to take an image of a bisque tile. When a user applies a glaze to the tile, the camera-computer system analyzes the glaze color among other factors affecting the painting process and an image showing a final color of the tile after firing is presented on the display of the computer system such that by looking at the computer screen, the user is able to see the actual final color of the tile after firing while applying the initial glaze to the bisque tile before firing.

18 Claims, 8 Drawing Sheets

PAINTING PROCESS COLOR COMPENSATOR

FIELD OF THE INVENTION

The present invention relates generally to information processing systems and more particularly to a methodology and implementation for determining painting process color changes.

RELATED APPLICATIONS

Subject matter disclosed but not claimed herein is disclosed and claimed in co-pending application 05-0947.

BACKGROUND OF THE INVENTION

Currently, when tiles are painted, the color of the glaze used bears almost no resemblance to the final color after the tile is fired in a kiln or furnace. It is very difficult for the painter to imagine the final product and get consistency from one tile to the next. Consequently, this process is extremely expensive today.

Many different factors affect the color of glaze after it is fired. First, the glazes are made of materials that significantly alter color when fired. For example, gold looks brown when it is painted on as a glaze. There are many factors that affect how the color will change. Such factors include glaze manufacturer, substrate color, temperature and length of firing, position in the kiln. All of these factors must be taken into account when deciding what compensation to make in order to arrive at a desired final or finished color of a tile after firing. In addition, glazes can be overlapped, applied several times, or applied unevenly in order to obtain a variation in the final color.

Thus, there is a need for an improved methodology and system for enabling consistent and repeatable determining of a final color for painting processes in which there is a color change from a starting color to a finished color.

SUMMARY OF THE INVENTION

A method and implementing computer system are provided for enabling a user to paint a surface a desired final color while using a paint, the color of which appears, in initial form, different from the desired final color for the painted surface. In an exemplary embodiment, a tile painting application is illustrated and includes a camera arranged to take an image of a bisque tile. When a user applies a glaze to the tile, the camera-computer system analyzes the glaze color among other factors affecting the painting process and an image showing a final color of the tile after firing is presented on the display of the computer system such that by looking at the computer screen, the user is able to see the actual final color of the tile after firing while applying the initial glaze to the bisque tile before firing.

BRIEF DESCRIPTION OF THE DRAWINGS

A better understanding of the present invention can be obtained when the following detailed description of a preferred embodiment is considered in conjunction with the following drawings, in which:

FIG. 3 is a flow chart illustrating an exemplary sequence of actions which may be used in painting a tile;

DETAILED DESCRIPTION

It is noted that circuits and devices which are shown in block form in the drawings are generally known to those skilled in the art, and are not specified to any greater extent than that considered necessary as illustrated, for the understanding and appreciation of the underlying concepts of the present invention and in order not to obfuscate or distract from the teachings of the present invention.

Figure 1:
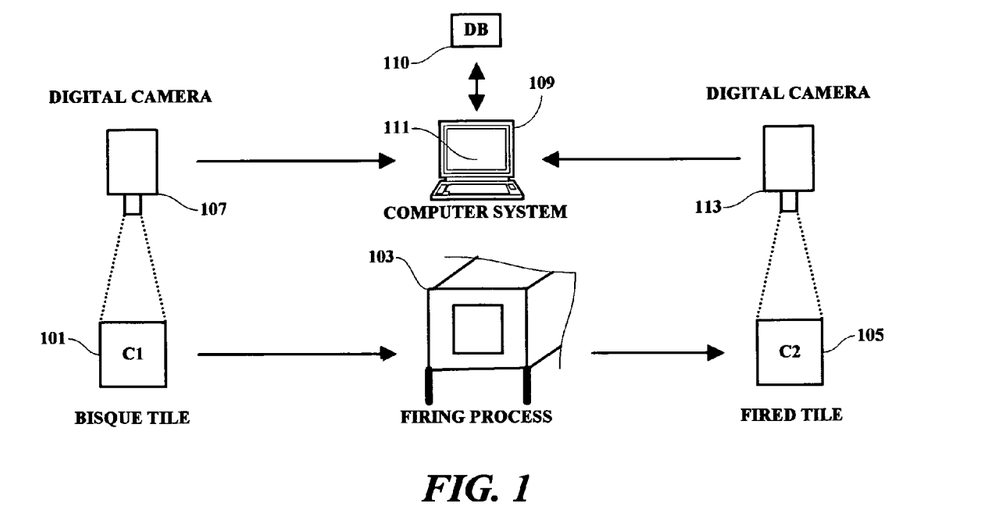
FIG. 1 is an illustration of an overall system in which the present invention may be implemented.

With reference to FIG. 1, there is shown an overall tile firing processing system in which the present invention may be implemented. As shown, a glazed starting or bisque tile 101 is shown as having a first color C1. That glazed bisque tile 101 is placed in a firing unit 103 under specified known firing conditions including temperature, firing time, etc., and after the firing process has been completed, the tile is removed from the process and shown as fired tile 105. After firing, the tile 105 exhibits a second color C2 which is different from the pre-fired glaze color C1. The firing process may be computer-controlled to insure compliance with a given set of firing conditions.

In one implementation, a digital color camera 107 is placed to selectively obtain a color image of the glazed bisque tile 101 before firing. The image of the glazed tile, including the color C1, is transmitted to a computer system 109 for processing. The initial color image is saved within a database (DB) 110 along with other information relating to the tile, the glaze and the firing process. All of only a portion of the database may be stored within the computer system or stored within a remote computer system accessible through an interconnection network. In one example, similar information including the color C2 of the fired tile 105 may also be obtained by a digital color camera 113 and transmitted to the computer system 109 for storage in the DB 110 and/or processing of the relevant information as is hereinafter explained. The system illustrated in FIG. 1 may also be used to obtain actual colors of pre-fired tiles using camera 107, and after-fired tiles using camera 105, and then saving the relationship between the pre-fired color C1 and the post-fired color C2 in a database DB 110 for access by subsequent users.

Figure 2:
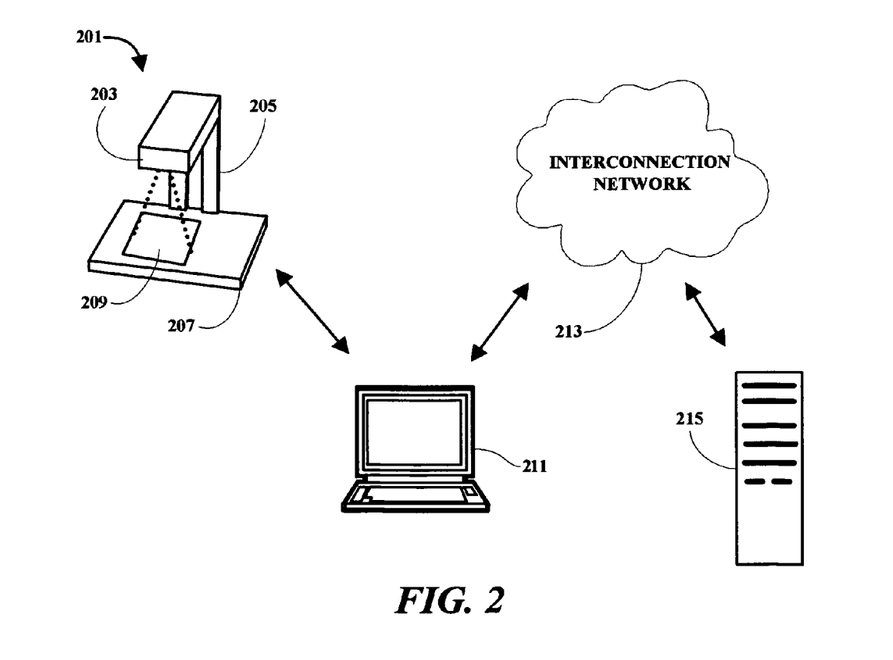
FIG. 2 is an illustration showing a specific implementation of an exemplary embodiment.

As shown in FIG. 2, the various methods discussed herein may be implemented within a specific system or network including a camera workstation 201 coupled to a computer device 211 which, in turn, is coupled through an interconnection network 213 such as the Internet, to a server 215. A camera 203 is arranged to be supported 205 in order to have a viewing angle as illustrated to view a tile 209 placed on a work table or surface 207. Images are selectively taken by the camera 203 and processed by the computer 211 along with additional information which may be downloaded from a remote server 115. As is hereinafter discussed, the camera workstation 201 also includes a motion detection system (not shown) which is used to determine when there is motion under the camera such as will occur as a painter moves a brush to paint the tile 209. Such motion detection is useful in determining the number of coats or layers of paint are being applied to a tile 209 during a painting process.

Figure 3:
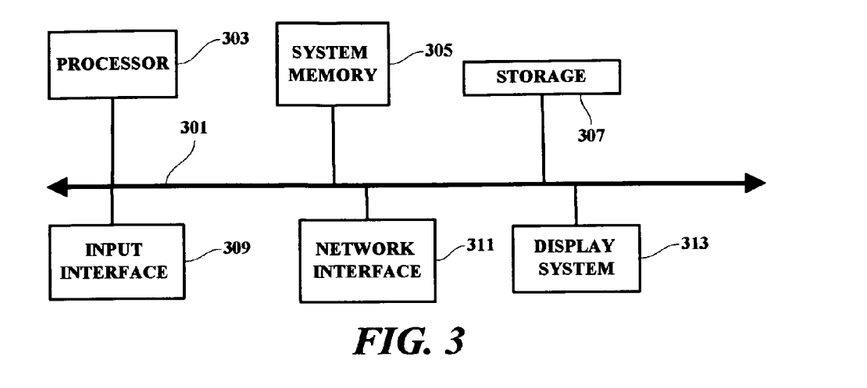
FIG. 3 is a block diagram showing several of the major components of a computer system shown in FIG. 1.

Several of the major components of the computer terminal 211 are illustrated in FIG. 3. A processor circuit 303 is connected to a system bus 301. It is noted that the processing methodology disclosed herein will apply to many different bus and/or network configurations. A system memory 305 and a storage unit 307 are also connected to the bus 301. An input interface 309 is also shown connected to the main bus 301. The input interface 309 enables a user or artist to input, by keyboard or menu-driven pointing device, certain information into the computer during a painting process. A network interface 311 enables the computer 211 to be coupled to a remote server 215 or any other information source which may be available on the World Wide Web using the Internet or other interconnection network. The computer 211 also includes a display system for displaying colors and other process related information, such as selection menus, to the user. In the present disclosure, the term "artist" is used on occasion and refers to a user who is operating the computer 211 in conjunction with painting a tile 209 or other painting surface.

Figure 4:
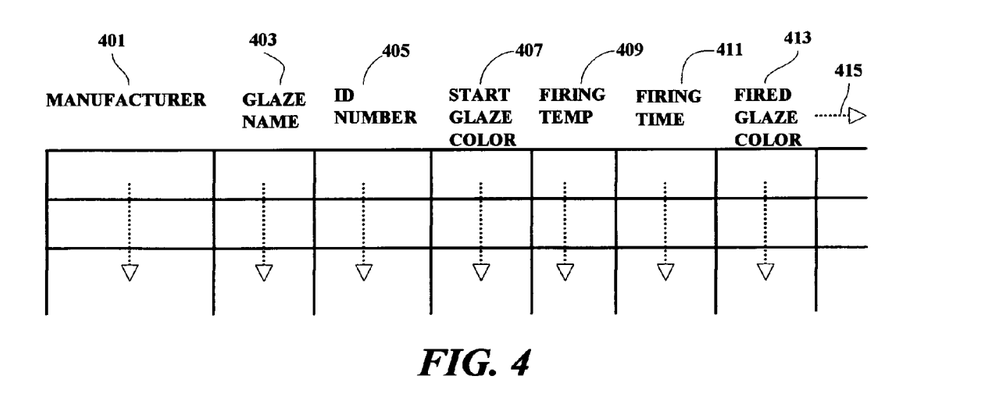
FIG. 4 is an illustration showing an exemplary database which may be used in practicing the present invention.

An exemplary painting color database (DB) is shown in FIG. 4. As shown, a comprehensive database 110 (FIG. 1) is stored in the computer 211 or is accessible by accessing the server 215. The painting database includes various parameters of the painting process such as the name of the manufacturer 401 of the glazes used for painting, the glaze name 403, an identification number (ID) 405 for the particular glazes, the starting or raw glaze colors 407, a firing temperature 409 for which the specified color changes would be valid, the firing time 411 or the time that the tile remains in the kiln, the fired or finished tile/glaze color 413, and other variables 415 which may be accessed and/or retrieved from the database in connection with the painting process. Typically, the glaze information is available from the manufacturer and the final colors for the painted surfaces are determined by the disclosed process, related to the other information regarding the process used and stored in the database column 413 for future referral and/or access and retrieval. As noted above, the painting database may be kept in storage in the computer 211, the server 215 or any other computer system accessible through an interconnection network 213.

Figure 5:
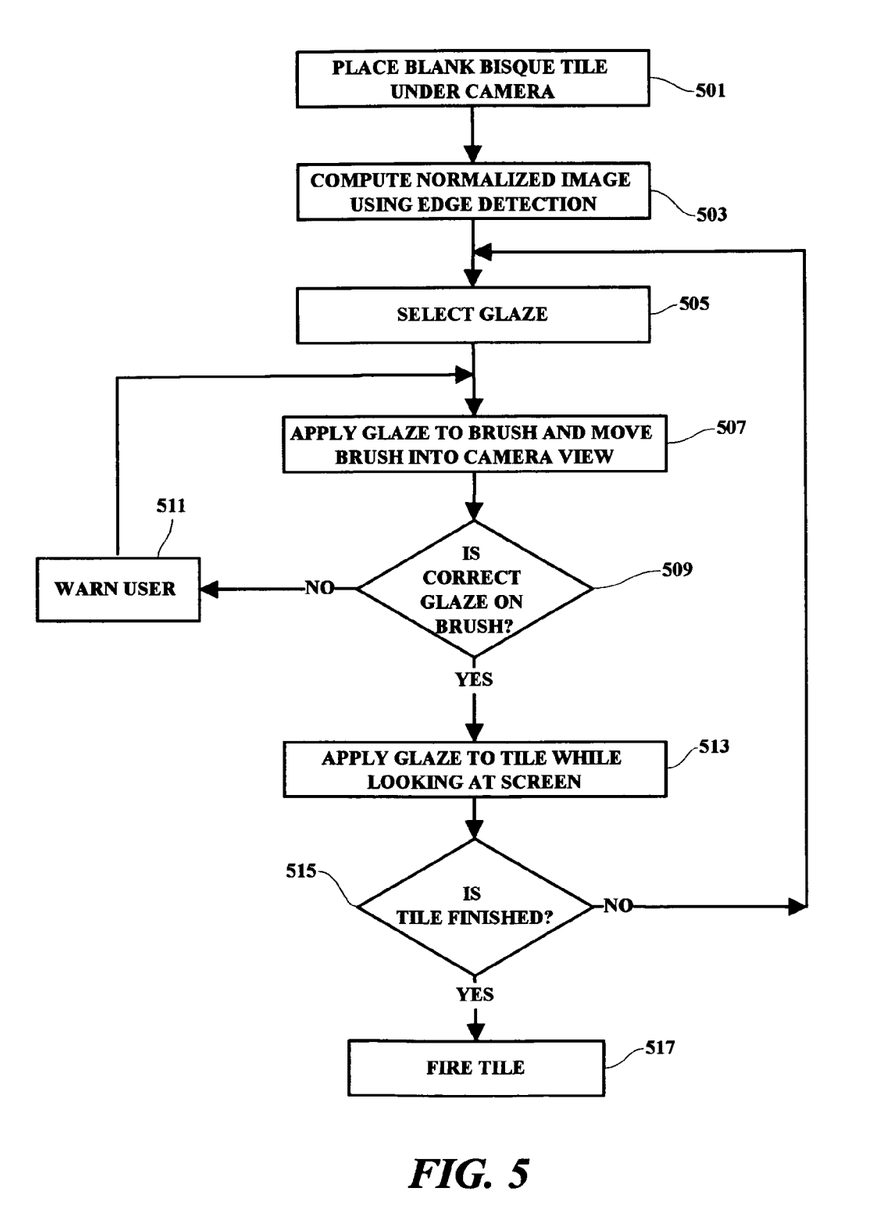
FIG. 5 is a flow chart illustrating a methodology for obtaining a color relationship between a starting tile color and a fired tile color.

Bisque tiles are tiles that have been fired but not glazed. Consequently they are rough and porous. This is the normal surface when painting tiles. The gloss seen on finished tiles is a transparent layer applied after the painting has been completed and before the tile is fired. As shown in FIG. 5, when the tile is placed 501 under the camera 203, the computer detects the edges of the tile and then displays the tile on the computer screen rotated so that its edges always appear parallel to the edges of the screen. In this manner, a normalized image of the tile is produced 503 using edge detection techniques. The normalized image is stored as a 1024×1024 pixel image in RGB format (Red Green Blue format). This has 256 shades each of red, green and blue and gives approximately 24 million different colors. This image is reduced in size for display purposes if the screen cannot display that many pixels. Good quality expensive screens can display that many pixels. Alongside an image of the tile on the display screen of the computer 211, a vertical display of glazes by manufacturer is presented (not shown). These will show the "before and after" colors, i.e. before the tile is fired and after the tile is fired. The user will select 505 which manufacturer and which glaze is to be used. The artist may also select custom glazes. The artist may also select custom profiles for color correction rather than rely on the manufacturer's specification for "before and after" colors. These custom profiles and custom colors are entered into the computer in a later part of the process. Glaze is then put on the painter's brush 507 and the brush is moved to a position within the camera viewing angle as shown in FIG. 2. If the camera does not see the color it expects 509, then the artist will get a warning 511 that there may be a mistake. The warning may be a displayed warning and/or an audible signal. Either the artist has put the wrong glaze on the brush, or the artist has selected the wrong glaze on the display screen. The artist will only look at the screen while applying glaze 513. The artist will actually see the finished color on the screen, i.e. the actual color of the tile after firing rather than the actual color of the glaze being painted on the tile. The computer will detect thinly and thickly applied glazes and will display the appropriate final color and effect (such as texture). The computer will also detect overlapping glazes and will show the final color and effect of the combination. Once the painting is complete 515, the tile is fired 517.

Figure 6:
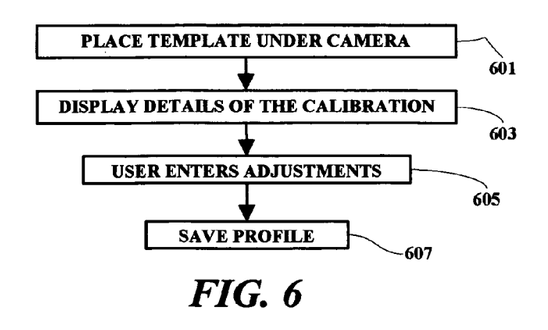
FIG. 6 is a flow chart illustrating a calibration technique used in association with the present invention.

Various calibrations on the manufacturer's colors can be accomplished by a user. As shown in FIG. 6, templates can either be produced by the manufacturer, or they can be made by the artist from the artist's own custom colors. A template may be placed 601 under the camera 203 and the displayed image shows several glazes and glaze colors. There is a display of the "before" and "after" color of each glaze and the manufacturer's number for the glaze. The artist can also produce templates for custom colors. These colors are then displayed on a palette 603 that is used by the artist to select a glaze when painting. The artist may wish to adjust the standard "before" and "after" colors 605 displayed by the manufacturer's templates. This can be done on the display screen through the input interface 309 by using the keyboard and/or pointing device. When adjustments are made, the artist can save these adjustments 607 as a profile for later use when painting tiles.

Figure 7:
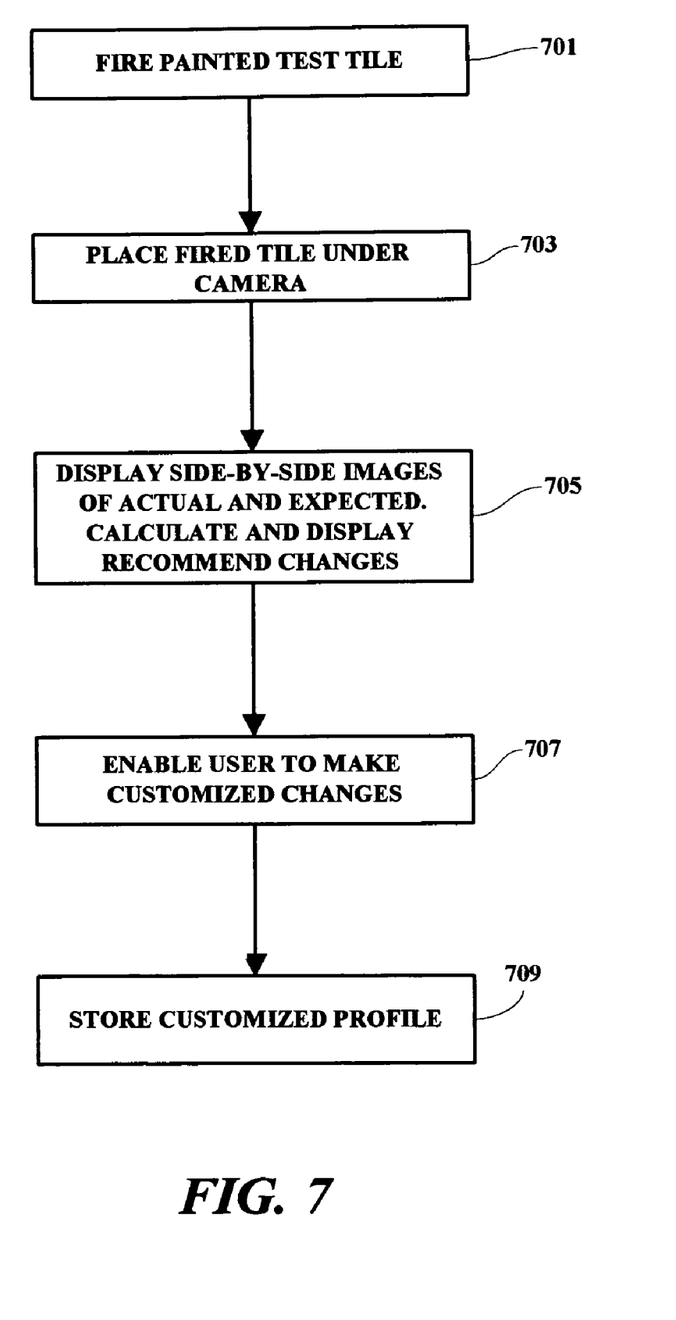
FIG. 7 is a flow chart illustrating a parameter feed-back technique which may be used in connection with the present invention.

Another feature of the present disclosure enables a user to adjust parameters using feedback from the camera system shown in FIG. 1 or FIG. 2. When a tile is fired, it may look a little different from the expected result. As shown in FIG. 7, in one example of using color feedback in changing color parameters, a test tile is fired 701 and the fired test tile is placed 703 under the camera 203 and a side by side image is produced 705 showing what the tile actually looks like compared with the computer prediction. The computer will calculate what adjustment needs to be made to each glaze and will display these adjustments. The artist can now either accept the computer changes or make the user's own changes 707 and save the results 709 as a profile for use in future tile painting projects.

This methodology may also be implemented for determining a starting glaze color for a tile from analysis of a fired glaze color of a tile. The method includes obtaining an image, including color, of a fired glaze color on a fired tile 105 by using, for example, a color digital camera 113, and then accessing a database DB 110 in a computer system 109 to determine information descriptive of the starting tile glaze color, e.g. C1, and related fired tile glaze color, e.g. C2, for glazes before and after being fired in a kiln, respectively. The starting glaze color C1 can thereby be determined by taking a picture of a fired tile color C2 and matching the fired tile color C2 with a fired tile color in a color database DB 110, and then retrieving the initial glaze color C1 identified in the database as corresponding to the fired tile color C2 as captured by the camera 105. Using this methodology, it may be determined that different glazes from different manufacturers may be used to obtain the same final or fired color for a given tile.

Figure 8:
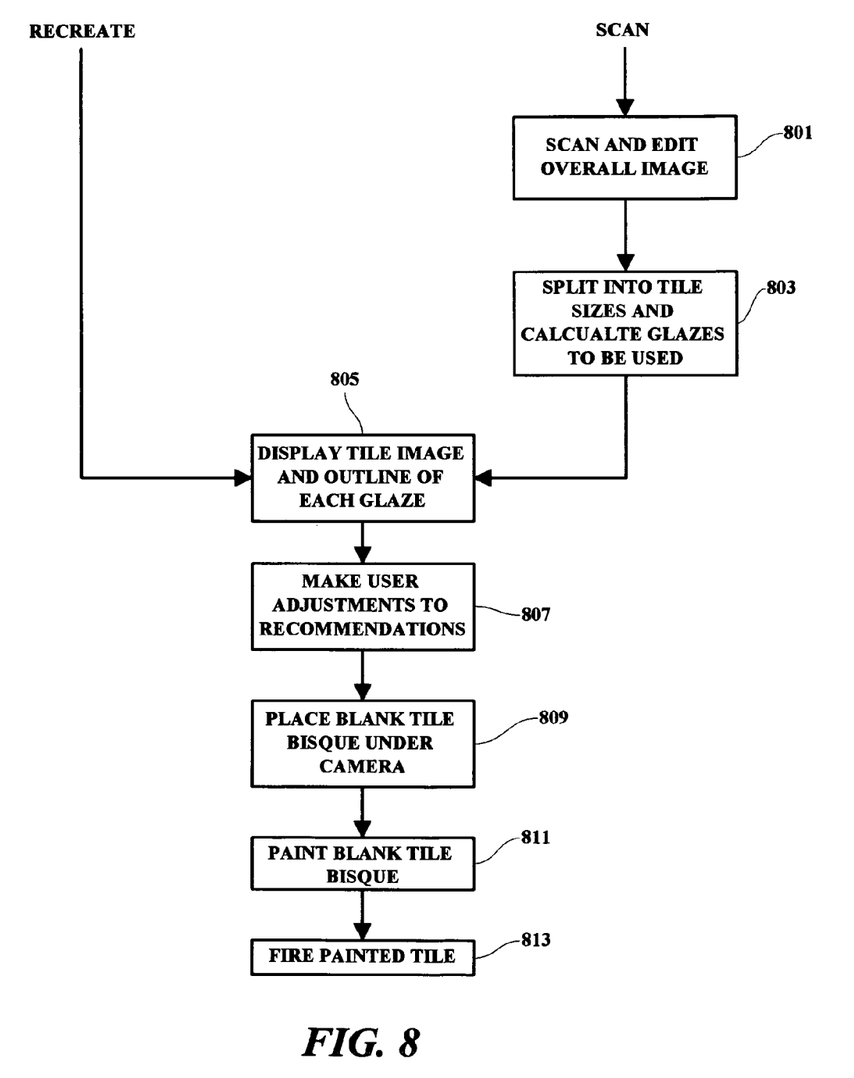
FIG. 8 is a flow chart illustrating an exemplary methodology for recreating a tile or producing a tile from a scanned image.

Another feature of the disclosed system enables a user to recreate a tile or produce a painted tile from a scanned image. There are several reasons why an artist may wish to recreate a tile. For example, the artist may make a mistake and wish to reproduce the tile quickly up to the point where the mistake was made. In another instance, the artist may not like the colors once the tile has been fired and wishes to reproduce the tile with slightly different glaze colors. Or, the artist may simply want to produce several hand painted replicas of a tile. The computer is able to produce an image of the tile with outlines and glaze numbers so that the artist can quickly reproduce the tile with a simple "painted by the numbers" type of approach. Alternatively, the artist may wish to paint an existing picture. An exemplary process is illustrated in FIG. 8. The picture to be painted on the tile must exist in digital form either by scanning the picture or taking an existing digital picture such as a photograph. This should be edited as required 801 before starting the process using any of many available color graphics applications. The computer will then split the picture into tile size pieces 803 and will calculate a "paint by the numbers" image for each tile using the profile of glazes that the artist selects. The image is displayed 805 and is ready for the artist to paint. Before starting, the artist can make any desired adjustments 807. For example, the artist can try "what if" experiments with glazes other than those selected by the computer and can see the predicted effect. The user then proceeds to place the tile 809 under the camera 107, paint the blank tile bisque 811 and fire the painted tile 813.

In the disclosed example, each pixel in the 1024×1024 internal image carries its own entire history. Each pixel will carry several parameters. For example, each pixel will be associated with a reference to the base color and texture of the underlying bisque, a reference to each layer of glaze that is used, a parameter indicating the thickness of each glaze layer and/or the current RGB value calculation for the finished, fired pixel. The tile image will also carry references to the profiles that should be used in color correction. The image is calculated from scratch and refreshed from scratch frequently. The RGB value is refreshed frequently. When glaze is applied, the computer detects where the glaze has been applied to the tile and recalculates and displays those pixels in real time. This eliminates any delay between what the artist sees on the screen, and what has actually happened to the tile. If glazes are white or almost white in color when first applied, the bisque can be painted or dipped in a dye that will be eliminated when the tile is fired. This can ensure there is a contrast between any glaze color and the tile background. The computer screen will always show the finished tile with the background dye removed.

Figure 9:
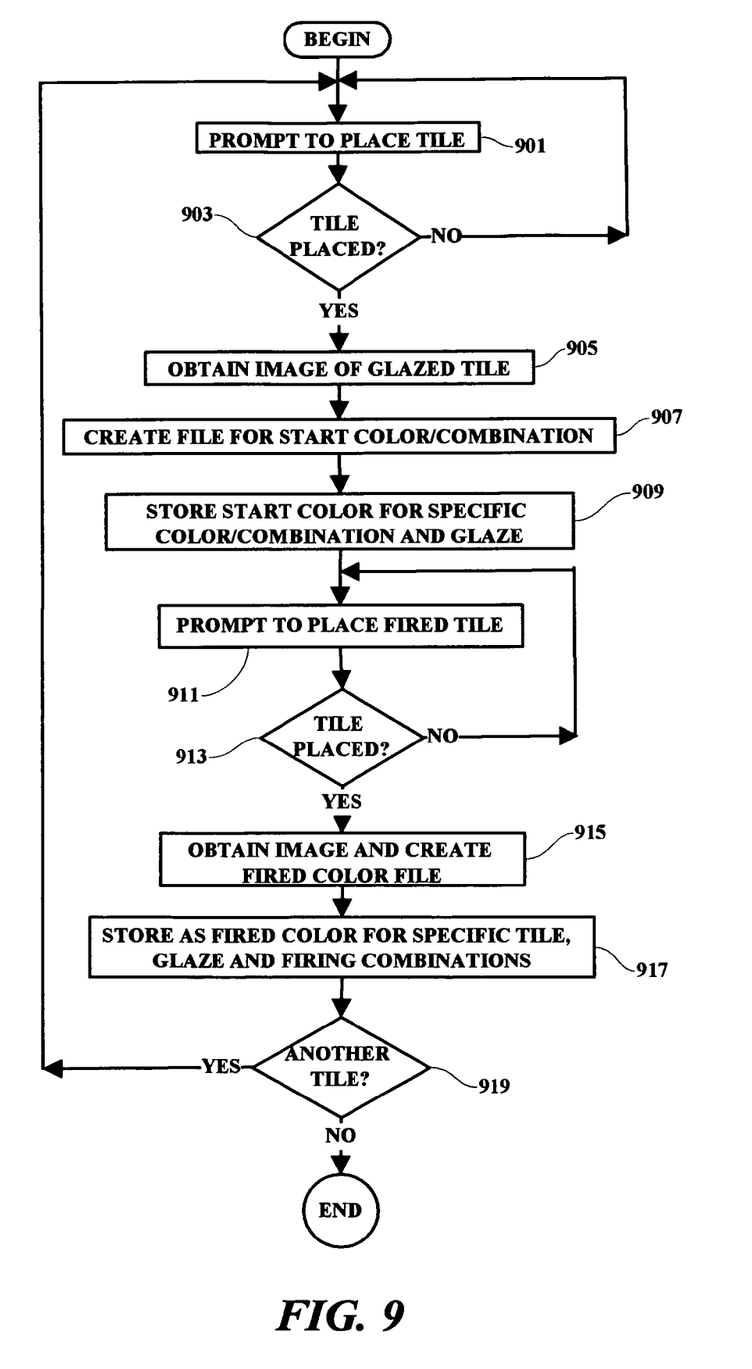
FIG. 9 is a flow chart illustrating a methodology for creating a database correlating actual glaze colors with actual fired colors for given tiles.

FIG. 9 shows an exemplary sequence for a program executing the methodology disclosed herein. As shown, initially a prompt is displayed 901 to a user to place a bisque tile 209 on the camera workstation 201. When it is detected that the user has placed the tile on the camera-viewable work surface, an image of the tile with the starting or initial glaze color is taken 905. A file is then created for the start color or color combination 907. As hereinbefore noted, the file includes user input information concerning the specific tile, firing characteristics etc., as well as the RGB color of the bisque tile which is provided by the camera 203. The start color is then stored 909. The user is then prompted 911 to place the fired tile (i.e. the glazed tile after it has been fired) under the camera. The user then places the fired tile under the camera 913 and the camera obtains an image and creates a fired or final color file 915. The system may determine that the fired tile has been placed under the camera either through user input to the computer or through a weight-detection or other automatic presence-detection device. The final color is then stored 917 in the database for the appropriate tile and process parameters, and the process is then repeated 919 for subsequent tiles.

Figure 10:
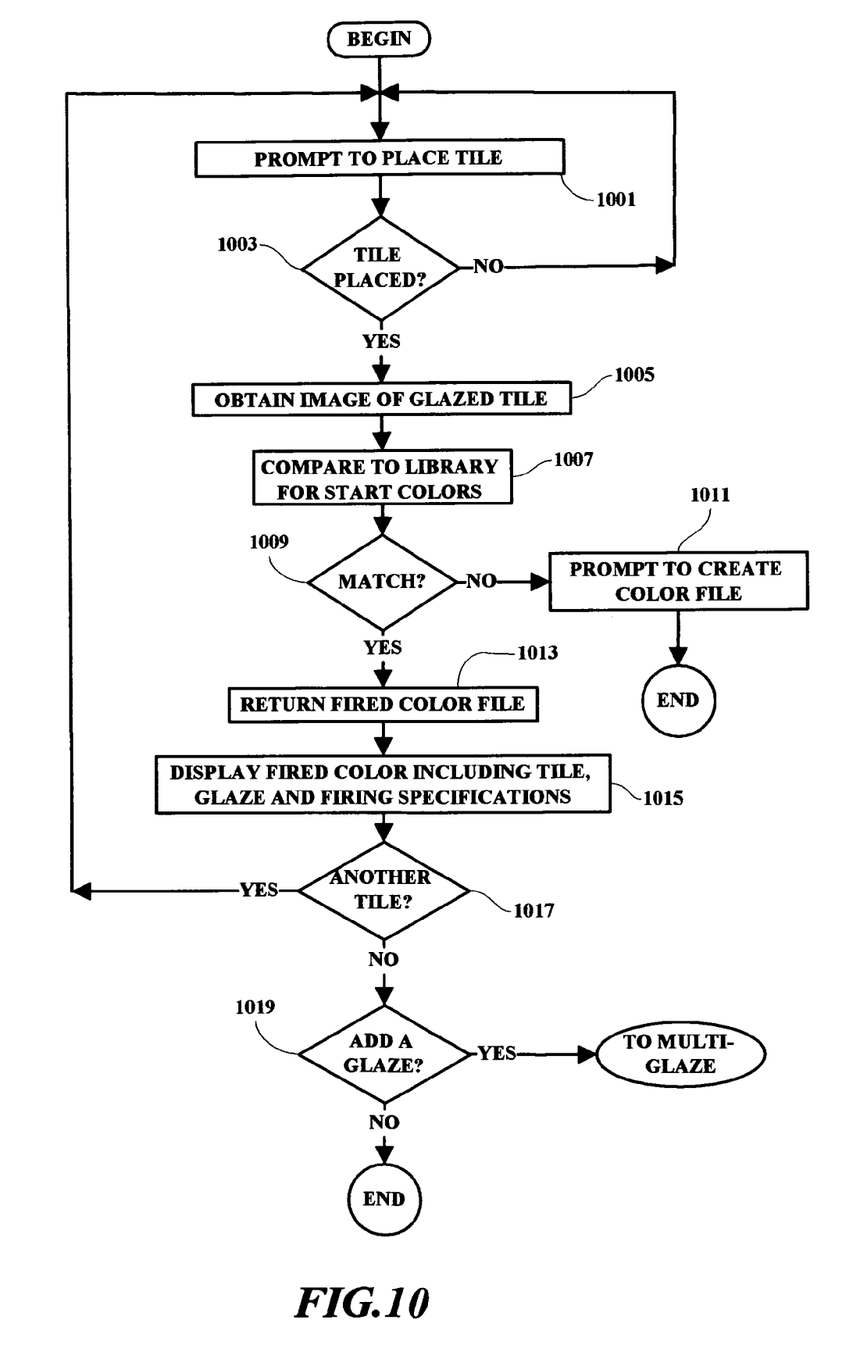
FIG. 10 is a flow chart illustrating a methodology for displaying a fired tile color to a user for a given tile glaze combination.

FIG. 10 shows an exemplary operational sequence for displaying a final tile color to a user. As shown, the user is prompted to place a bisque tile 1001 and when the tile is placed 1003 an image of the glazed bisque tile is obtained 1005. The color detected by the camera is compared 1007 to the start color library or database, and if there is no match, i.e. the color has not been previously processed, the user is prompted to create a color file 1011. If the color of the glaze can be matched to a starting color in the database 1009, then the fired color for the detected start color is retrieved 1013 and displayed to the user 1015. This display may also include all or a portion of the other data items in the database which are related to the working tile. The process will repeat 1017 for additional tiles for which the user wishes to view the finished color. If the user wishes to add another glaze to the tile 1019, the program executes a multi-glaze routine as shown in FIG. 11.

Figure 11:
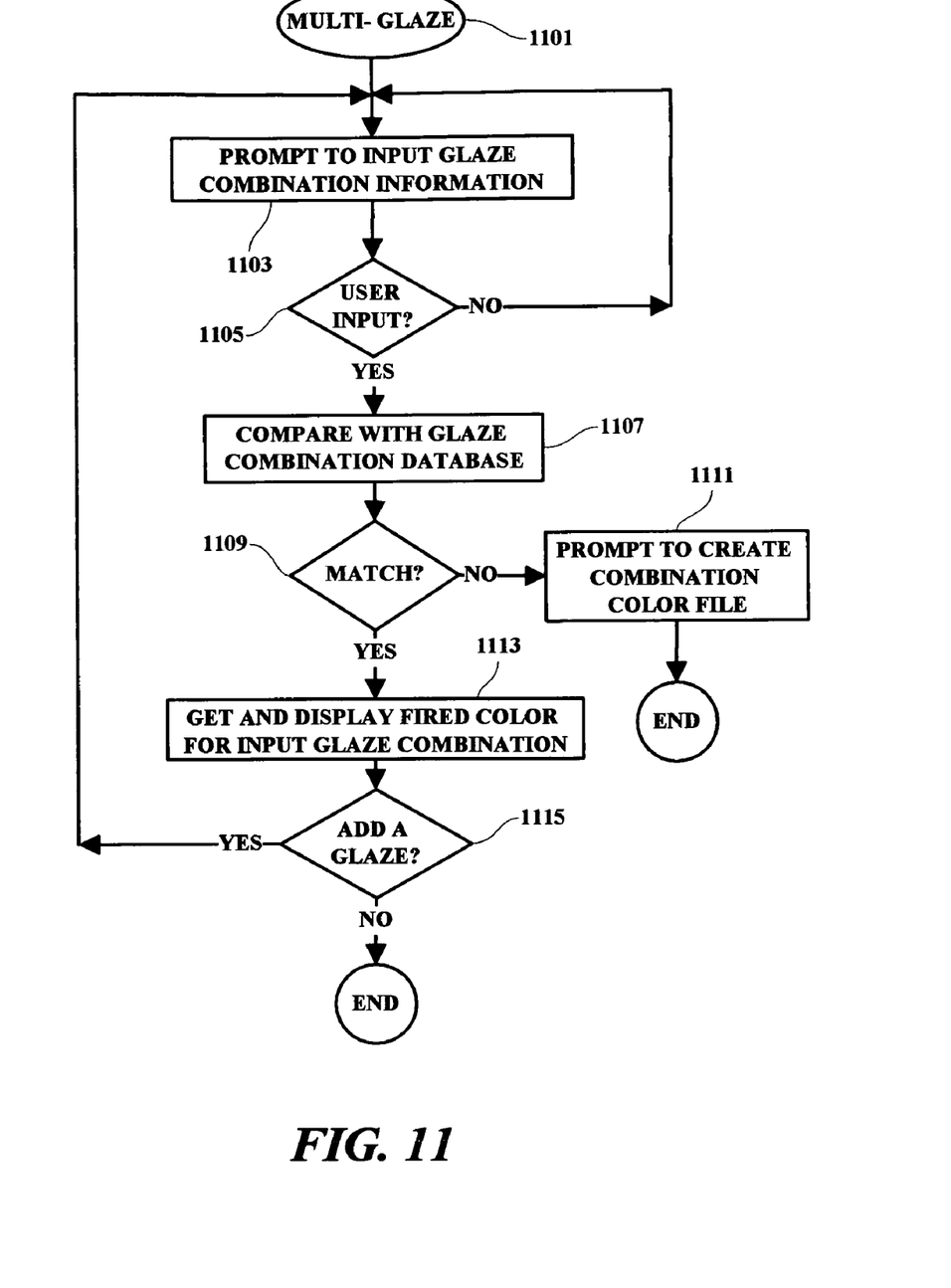
FIG. 11 is a flowchart illustrating a methodology for creating combination color files and/or displaying fired tile color for user specified glaze combination information.

In FIG. 11, a multi-glaze feature initially prompts a user to input glaze combination database information 1103. After all of the fields have been entered by the user 1105, a comparison is made to a glaze combination database 1107 and if the particular glaze combination has been processed and recorded before 1109, the final color for the combination glaze is retrieved and displayed 1113 to the user. If there is no match 1109 the user is prompted to create a combination color file 1111 by taking a picture of the initial combination glaze, firing the tile and recording the final color in relationship or association to the beginning combination color. This process may be repeated for additional glazes 1115 which may be added to the tile.

Although the examples presented herein refer to a tile painting process, it is understood that the concepts presented may also be applied to any painting process wherein the initial painting color undergoes a change in color during a process used to produce a final or finished product. For example, the color processing methodology disclosed herein may also be applied to surface painting in general to enable a painter to see a finished color or result by inputting painting variables such as paint manufacturer, name of the paint color being used, surface type, surface temperature, primer information, number of coats etc., to a computer and viewing the final color that will be produced on the surface being painted.

The method and apparatus of the present invention has been described in connection with a preferred embodiment as disclosed herein. The disclosed methodology may be implemented in a wide range of sequences, menus and screen designs to accomplish the desired results as herein illustrated. Although an embodiment of the present invention has been shown and described in detail herein, along with certain variants thereof, many other varied embodiments that incorporate the teachings of the invention may be easily constructed by those skilled in the art, and even included or integrated into a processor or CPU or other larger system integrated circuit or chip. The disclosed methodology may also be implemented solely or partially in a programmed product or program code stored on a CD, disk or diskette (portable or fixed), or other memory device, from which it may be loaded into memory and executed to achieve the beneficial results as described herein. Accordingly, the present invention is not intended to be limited to the specific form set forth herein, but on the contrary, it is intended to cover such alternatives, modifications, and equivalents, as can be reasonably included within the spirit and scope of the invention.

What is claimed is:

1. A method for determining a color of a first surface of an object after said first surface has been painted with a coating substance of a first color and subjected to a painting-related process operable to effect a change from said first color to a second color, said method comprising:
    using a camera to take a picture of said coating substance as said coating substance is being applied to a first area of said object before said object is subjected to said painting-related process;
    determining said first color from said picture;
    accessing paint process information concerning said painting-related process from a computer system coupled to said camera;
    processing said paint process information and said first color by said computer system to determine said second color; and
    displaying said first area of said object on a display device as said coating substance is applied to said first area, said first area being displayed on said display device being colored with said second color.

2. The method as set forth in claim 1 and further including:
    defining relationship information between said first color, said second color and said paint process information; and
    saving said relationship information in a process color change file accessible by said computer system.

3. The method as set forth in claim 2 and further including accessing said process color change file after said saving.

4. The method as set forth in claim 3 wherein said object is a tile to be painted, said coating substance is a glaze and said painting-related process is the firing of said tile in a kiln after said first surface has been painted with said coating substance, and wherein said processing by said computer system includes using said information input by said user to access a database and retrieve said second color from said database corresponding to said first color and said information input by said user.

5. The method as set forth in claim 4 wherein said database includes information related to a designated temperature at which said kiln is maintained.

6. The method as set forth in claim 4 wherein said database includes information related to a designated time period during which said object remains in said kiln.

7. The method as set forth in claim 4 wherein said database includes information related to a manufacturer of said object.

8. The method as set forth in claim 4 wherein said database includes information related to an identification of said coating substance.

9. The method as set forth in claim 1 wherein said method is embodied in a programmed product, said programmed product being selectively effective when installed on a computer system for:
    prompting a user to take a picture of said coating substance applied to said object before said object is subjected to said painting-related process, said picture including making a determination of said first color;
    enabling a user to input information concerning said painting-related process into a computer system coupled to said camera;
    processing said information by said computer system to determine said second color; and
    displaying said second color on a display device of said computer system.

10. A method for creating a database for a painting system in which a bisque tile having a first color on a first surface is painted with a coating substance and subjected to a firing process operable to effect a change from said first color to a second color, said method comprising:
    using a camera to take a picture of said coating substance as said coating substance is being applied to said first surface of said bisque tile, said picture including making a determination of said first color;
    firing said bisque tile in a kiln for a predetermined time and predetermined temperature to produce a fired tile, wherein said first color of said bisque tile changes to a second color on said first surface of said fired tile during said firing;
    using a camera to take a picture of said first surface of said fired tile, said picture including making a determination of said second color; and
    relating said first color to said second color in a database, said database being stored in a computer system coupled to said camera.

11. A computer system for determining a color of a first surface of an object after said first surface has been painted with a coating substance of a first color and subjected to a painting-related process operable to effect a change from said first color to a second color, said computer system comprising:
    a system bus;
    a CPU device connected to said system bus;
    an input device connected to said system bus, said input device being arranged to enable user input to said computer system;
    a display device connected to said system bus;
    means arranged for coupling said computer system to a camera device, said camera being selectively operable to take a picture of said coating substance as said coating substance is being applied to said object before said object is subjected to said painting-related process, said picture including making a determination of said first color, said system being further operable for accessing information concerning said painting-related process, said computer system being operable for processing said information to determine said second color, said display device being operable for displaying said second color to said user as said coating substance of said first color is being applied to said object.

12. The computer system as set forth in claim 11 and further including means for defining relationship information between said first color, said second color and said paint process information, and means for saving said relationship information in a process color change file accessible by said computer system.

13. The computer system as set forth in claim 12 and further including means for accessing said process color change file after said saving.

14. The computer system as set forth in claim 13 wherein said object is a tile to be painted, said coating substance is a glaze and said painting-related process is the firing of said tile in a kiln after said first surface has been painted with said coating substance, and wherein said processing by said computer system includes using said information input by said user to access a database and retrieve said second color from said database corresponding to said first color and said information input by said user.

15. The computer system as set forth in claim 14 wherein said database includes information related to a designated temperature at which said kiln is maintained.

16. The computer system as set forth in claim 14 wherein said database includes information related to a designated time period during which said object remains in said kiln.

17. The computer system as set forth in claim 14 wherein said database includes information related to a manufacturer of said object.

18. The computer system as set forth in claim 14 wherein said database includes information related to an identification of said coating substance.

* * * * *